United States Patent [19]

Wu et al.

[11] Patent Number: 5,254,791
[45] Date of Patent: Oct. 19, 1993

[54] CYCLOALKANE ISOMERIZATION PROCESS

[75] Inventors: An-hsiang Wu; Lyle R. Kallenbach; Marvin M. Johnson, all of Bartlesville, Okla.

[73] Assignee: Phillips Petroleum Company, Bartlesville, Okla.

[21] Appl. No.: 10,372

[22] Filed: Jan. 28, 1993

[51] Int. Cl.$^5$ ............................................... C07C 5/29
[52] U.S. Cl. .................................... 585/372; 585/373; 585/375
[58] Field of Search ............... 585/372, 373, 375, 374; 502/202, 208, 217, 231

[56] References Cited

U.S. PATENT DOCUMENTS

| | | | |
|---|---|---|---|
| 2,824,153 | 2/1958 | Kelly et al. | 585/726 |
| 3,248,343 | 4/1966 | Kelly et al. | 252/442 |
| 3,271,299 | 9/1966 | Kearby | 208/114 |
| 3,873,634 | 3/1975 | Hoffman | 585/726 |
| 3,925,495 | 12/1975 | Rodewald | 585/373 |
| 4,094,922 | 6/1978 | Bartek et al. | 260/671 C |

*Primary Examiner*—Asok Pal
*Attorney, Agent, or Firm*—K. K. Brandes

[57] ABSTRACT

$C_5$-$C_{10}$ cycloalkanes (preferably methylcyclopentane) are isomerized in the presence of a catalyst comprising aluminum chloride and at least one of the following materials: boron phosphate on silica, boron phosphate on activated carbon, boron sulfate on silica.

14 Claims, No Drawings

CYCLOALKANE ISOMERIZATION PROCESS

BACKGROUND OF THE INVENTION

This invention relates to the isomerization of cycloalkanes.

The use of supported aluminum chloride catalysts for alkane isomerization is known. The present invention is directed to the use of novel, effective $AlCl_3$-containing catalyst materials for cycloalkane isomerization.

SUMMARY OF THE INVENTION

It is an object of this invention to employ materials prepared from aluminum chloride and select boron compounds as catalysts for isomerizing cycloalkanes. Other objects and advantages will be apparent from the detailed description of the invention and the appended claims.

In accordance with this invention, a process for isomerizing cycloalkanes comprises contacting, at a reaction temperature of about 0°–100° C., at least one cycloalkane containing 5–10 carbon atoms per molecule with a solid catalyst composition at effective isomerization conditions;

wherein said catalyst composition bas been prepared by a method comprising the steps of (I) heating in the substantial absence of water, at a temperature of about 40°–90° C., a mixture comprising (a) aluminum chloride, (b) at least one solid boron-containing material selected from the group consisting of boron phosphate on silica, boron phosphate on carbon and boron sulfate on silica, and (c) at least one cblorinated hydrocarbon having a normal boiling point (i.e., the boiling point at 1 atm. pressure) of about 40°–90° C., wherein the weight ratio of $AlCl_3$ to said at least one solid boron-containing material is at least about 0.25:1; and (II) separating the solid material contained in the reaction mixture obtained in step (I) from said at least one chlorinated hydrocarbon under a dry gas atmosphere.

In one preferred embodiment, the weight of $AlCl_3$ to the solid boron-containing material is about 0.5:1 to about 1.0:1. In another preferred embodiment, the isomerization reaction temperature is about 20°–50° C. In a further preferred embodiment, the feed cycloalkane is methylcyclopentane, which is isomerized to cyclohexane at a high selectivity (about 90–100%).

DETAILED DESCRIPTION OF THE INVENTION

Preparation step (I) can be carried out in any suitable manner. Generally, substantially dry agents (a), (b) and (c), which are all defined above, are thoroughly mixed under a dry gas atmosphere (preferably a dry inert gas atmosphere, e.g., $N_2$, He, Ar and the like), and the obtained mixture is then heated under a dry inert gas atmosphere at a temperature of about 40°–90° C., preferably about 70°–80°C., for a time period of about 4 to about 120 hours, preferably about 10–30 hours. It is preferred to carry out step (I) with agitation, either mechanically (e.g., by means of a stirrer) or ultrasonically. The weight ratio of (a) to (b) generally is about 0.25:1 to about 1.5:1. When material (b) is $BPO_4$/$SiO_2$ or $B_2(SO_4)_3$/$SiO_2$, this weight ratio preferably is about 0.25:1 to about 1.0:1. When material (b) is $BPO_4$/carbon, this weight ratio preferably is about 0.5:1 to about 1.0:1.

In one embodiment, the solid material (b) contains about 20 to about 80 weight-% (preferably about 23–65 weight-%) $BPO_4$ and/or $B_2(SO_4)_3$ and about 20–80 weight-% silica carrier (preferably about 35–73 weight-% $SiO_2$). In another embodiment, $BPO_4$ is the boron compound and activated carbon is used as the carrier (in lieu of silica), generally at a level of 20–80 weight-% carbon (preferably about 50–80 weight-% carbon). The surface area (measured by the BET method by Brunauer, Emmett and Teller employing nitrogen) of these solid materials (b) generally is in the range of about 100 to about 1000 $m^2$/g (preferably about 200–500 $m^2$/g). Preferably, the support particles have a size in the range of smaller than 20 mesh and larger than 60 mesh.

Preferably, the solid $BPO_4$-containing materials are prepared by the reaction of a boric acid ester, $B(OR)_3$, wherein each R can be independently selected from the alkyl radicals containing 1–5 carbon atoms (more preferably tri-n-propyl borate), and orthophosphoric acid ($H_3PO_4$), in the presence of silica or, alternatively, activated carbon, which are present during this reaction in an amount as to provide a material containing about 20–80 weight-% $SiO_2$ or, alternatively, 20–80 weight-% activated carbon. When a solid $B_2(SO_4)_3$-containing material is used as material (b), it is preferably prepared by the reaction of a boric acid ester (such as tri-n-propyl borate) and sulfuric acid, in the presence of silica at an amount to provide a level of about 80 weight-% $SiO_2$ in the $B_2(SO_4)_3$/$SiO_2$ material. The thus-obtained solid materials are then separated from the liquids by distillation, substantially dried and calcined (generally for about 2–5 hours at a temperature of about 250°–500° C., either in air or in a $N_2$ atmosphere) before they are employed in step (I).

Agent (c) used in step (I) is a chlorinated hydrocarbon or a mixture of two or more chlorinated hydrocarbons having a normal boiling point in the range of about 40°–90° C., preferably about 70°–80° C. Preferred chlorinated hydrocarbons are chlorine derivatives of paraffins. Non-limiting examples of suitable chlorinated hydrocarbons are dichlorometbane, chloroform (trichloromethane), carbon tetrachloride, 1,1-dichloroethane, 1,2-dicbloroethane, 1,1,1-trichloroethane, 1,1-dichloropropane, 2,2-dichloropropane, 1-chlorobutane, 2-chloro-2-methylbutane, and mixtures thereof. The preferred chlorinated hydrocarbon is carbon tetrachloride. Generally the ratio of the weight of the cblorinated hydrocarbon(s) to the combined weight of materials (a) and (b) employed in step (I) is about 4:1 to about 20:1.

Separation step (II) can be carried out in any suitable manner. Preferably, the finished reaction mixture obtained in step (I) is filtered, and the solid filter cake is substantially dried at any suitable conditions, preferably at subatmospheric (i.e., vacuum) conditions, at a temperature of about 25°–60° C. Preferably, step (II) is carried out under a dry inert gas atmosphere ($N_2$, He, Ar, and the like). The finished/dried catalyst particles should be stored under a dry inert gas atmosphere.

The catalyst composition prepared by the above-described preparation method is employed as a catalyst for isomerizing $C_5$–$C_{10}$ cycloalkanes, preferably methyl-substituted cycloalkanes, to product cycloalkanes (i.e., cycloalkanes having the same number of carbon atoms as the feed cycloalkanes by different structural formulas). Nonlimiting examples of suitable feed cycloalkanes are methylcyclobutane, methylcyclopentane, 1,1-dimetbyleyclopentane, 1,2-dimethylcyclopentane, 1,3-dimetbylcyclopentane, metbylcyclohexane, 1,1-dimethylcyclohexane, 1,2-dimethyleyclohexane, 1,3- dimethylcyclohexane, ethylcyclobexane, methylcyclobeptane, 1-methyl-2-ethylcyclopentane, 1,1-dimethylcycloheptane, 1,2-dimethylcycloheptane, 1,3-dimetbylcyclobeptane, ethylcycloheptane, 1-methyl-2-etbylcyclohexane, methylcyclooctane, 1,1-dimetbylcyclooctane, 1,2-dimethylcyclooctane, 1,3-dimethylcyclooctane, and mixtures thereof. The preferred cycloalkane is methylcyclopentane which is substantially completely converted to cyclohexane.

The process for isomerizing $C_5$–$C_{10}$ cycloalkanes with at least one of the above-described catalyst compositions can be carried out under any suitable reaction conditions at a relatively low temperature of up to about 100° C., more preferably about 20°–50° C. (most preferably about 30°–40° C.), generally at about 1–5 atm. pressure, for about 0.1–8 hours. The feed hydrocarbon(s) can be contacted with the catalyst composition in any suitable mode, such as in a slurry operation in which the catalyst is dispersed in the feed hydrocarbon(s), or in a fixed catalyst bed operation in which the hydrocarbon feed flows upward or downward through a solid catalyst layer (or several catalyst layers). The time of contact between the feed hydrocarbon(s) and the catalyst composition generally is in the range of about 5 minutes to about 8 hours, preferably about 1–2 hours. Each isomerization process can be carried out as a batch operation or as a continuous operation. Moisture is to be substantially absent during the isomerization process.

Since the isomerization process of this invention may generate more than one hydrocarbon product, it is generally necessary to separate the various formed hydrocarbons from one another and also from unconverted feed cycloalkane(s). This separation can be carried out in any suitable manner, generally by fractional distillation (possibly in the presence of an extractant, i.e., by extractive distillation), as is easily determined by persons skilled in the various liquid-liquid separation technologies.

The following examples are presented to further illustrate the invention and are not to be construed as unduly limiting the scope of the invention.

EXAMPLE I

This example illustrates the preparation of catalyst materials which were employed in cycloalkane isomerization tests.

Control Catalysts A1–A6 were prepared by beating various amounts of dry $AlCl_3$ and G-57 silica (20–40 mesh; BET/$N_2$ surface area: 340–350 m$^2$/g; marketed by Davison Catalyst Division of W. R. Grace and Company, Baltimore, MD, under the product designation of G-57; calcined for 4 hours at 550° C.) and 30 mL of dry $CCl_4$ for 18 hours under reflux conditions in the dark, under a $N_2$ gas atmosphere. The thus-heated mixture was cooled and then dried at about 30° C. under vacuum conditions. The amounts of $AlCl_3$ and $SiO_2$ were as follows: 0.373 g $AlCl_3$ and 1.50 g $SiO_2$ for Catalyst A1, 0.640 g $AlCl_3$ and 1.50 g $SiO_2$ for Catalyst A2, 0.896 9 $AlCl_3$ and 1.50 g $SiO_2$ for Catalyst A3, 1.78 g $AlCl_3$ and 2.50 g $SiO_2$ for Catalyst A4, 1.493 g $AlCl_3$ and 1.50 g $SiO_2$ for Catalyst A5, and 2.240 g $AlCl_3$ and 1.5 g $SiO_2$ for Catalyst A6.

Control Catalysts B1–B4 were prepared by heating various amounts of dry $AlCl_3$ and 1.50 grams $BPO_4$ (20–40 mesh; prepared by adding tri-n-propyl borate dropwise to phosphoric acid containing 85 weight-% $H_3PO_4$ and 15 weight-% $H_2O$, at a $(C_3H_5)_3B$:$H_3PO_4$ molar ratio of about 1:1, maintaining the reaction mixture at about 65°–80° C. for about 1 hour under a $N_2$ gas atmosphere, followed by distillation at about 110° C. for the removal of n-propanol and of water, and drying the solid $BPO_4$ reaction product under vacuum conditions at 120° C. for 3 hours) and 30 mL of dry $CCl_4$ for 18 hours under reflux conditions, followed by drying as described above for Catalysts A1–A6. The amounts of employed $AlCl_3$ were: 0.373 grams, 0.640 grams, 0.896 grams and 1.493 grams, respectively, for Catalysts B1, B2, B3 and B4, respectively.

Catalysts C1–C4 were prepared as follows. First, a $BPO_4$/$SiO_2$ materials containing 27 weight-% $BPO_4$ was prepared by mixing 34.35 grams of calcined 20–40 mesh G-57 silica (described above) and 1-3.8 grams of a mixture of aqueous 85 weight-% $H_3PO_4$ (described above), heating the mixture to about 80° C. under a $N_2$ atmosphere, adding dropwise with stirring 22.70 g tri-n-propyl, beating the entire reaction mixture for 2 hours under reflux conditions, thereafter distilling off essentially all liquids (mainly formed propanol and water) at a temperature of about 120° C., and finally drying the solid $BPO_4$ residue for 3 hours at a temperature of about 150° C. under vacuum conditions. 2.50 grams of the thus obtained $BPO_4$ on $SiO_2$ Material (containing 27 weight-% $BPO_4$) was then heated with $AlCl_3$ and $CCl_4$ and dried (as described for Catalysts A1–A6). The amounts of $AlCl_3$ were 0.622 grams, 1.245 grams, 1.867 grams and 2.489 grams, respectively, for Catalysts C1, C2, C3 and C4 respectively.

Catalysts D1–D3 were prepared as follows. First, a $BPO_4$/$SiO_2$ support material containing 75 weight-% $BPO_4$ was prepared essentially in accordance with above-described procedure for preparing $BPO_4$/$SiO_2$ (containing 27 weight-% $BPO_4$), except that the amount of added silica was adjusted to about 25 weight-% $SiO_2$ of the entire support material, which was heated for 2 hours at 300° C. in air. 1.50 grams of this $BPO_4$/$SiO_2$ material containing 75 weight-% $BPO_4$ was then heated with various amounts of $AlCl_3$ and $CCl_4$ and dried, as described for Catalysts A1–A6. The amounts of $AlCl_3$ were 0.373 grams, 0.747 grams and 1.120 grams, respectively, for Catalysts D1, D2 and D3, respectively.

Catalysts E1–E3 were prepared as follows. First 36.35 grams of Nuchar ® C activated carbon (Grade WV-B 14×35; obtained from Westvaco Chemical Division, Covington, VA; calcined under $N_2$ at 400° C. overnight) was mixed with 27.9 grams of aqueous 85 weight-% $H_3PO_4$ (described above), heating this mixture with stirring to 80° C. for 1 hour, adding dropwise 45.14 grams of tri-n-propyl borate to the hot mixture, increasing the temperature of the entire mixture to 120° C. over a 4 hour period, distilling of formed n-propanol and water at 130° C. for 1 hour, and finally drying the $BPO_4$/carbon material containing about 25 weight-% $BPO_4$ and about 75 weight-% C. 1.50 grams of this $BPO_4$/C material was heated with various amounts of $AlCl_3$ and 30 mL dry $CCl_4$ and then dried, as described for Catalysts A1–A6. The amounts of $AlCl_3$ were 0.373 grams, 0.747 grams and 1.120 grams, respectively, for Catalysts E1, E2 and E3, respectively.

Catalysts F1–F3 were prepared as follows. First, a $B_2(SO_4)_3$/$SiO_2$ support material containing 35 weight-% $B_2(SO_4)_3$, was prepared by mixing and beating (with stirring) 22.70 grams of tri-n-propyl borate, 17.76 grams of 100% $H_2SO_4$ and 34.35 grams of G-57 silica (described above) for about 2 hours at 80° C., then heating the reaction mixture to 120° C., distilling off liquids (mainly formed propanol) at about 120° C., and heating the solid residue in air at 275° C. for 2 hours. 1.50 grams of this $B_2(SO_4)_3/SiO_2$ material (containing 35 weight-% $B_2(SO_4)_3$ and 65 weight-% $SiO_2$) was then heated with various amounts of $AlCl_3$ and $CCl_4$ and finally dried, as described for Catalysts A1-A6. The amounts of $AlCl_3$ were 0.373 grams, 0.747 grams and 1.120 grams, respectively, for Catalysts F1, F2 and F3, respectively.

EXAMPLE II

This example illustrates the isomerization of methylcyclopentane to cyclohexane in the presence of the Catalyst materials described in Example I. All reactions were carried out at about 38°-40° C. in sealed ampules under a dry nitrogen atmosphere, employing about 10 mL of the feed hydrocarbon (methylcyclopentane) and about 0.5 grams of each of the catalysts. The reaction mixtures were slightly agitated for about 1-2 hours by means of an ultrasonic vibrator, and were analyzed by means of a gas chromatograph. Test results obtained after a reaction time of 1 hour are summarized in Table I.

TABLE I

| Catalyst Employed | Catalyst Preparation Method | | % Conversion of Methylcyclopentane | Selectivity to Cyclohexane[3] |
|---|---|---|---|---|
| | Support | Grams $AlCl_3$ per Gram Support | | |
| A1 | $SiO_2$ | 0.25 | 4.4 | 85.2% |
| B1 | $BPO_4$ | " | 8.8 | 92.7% |
| C1 | $BPO_4/SiO_2$[1] | " | 14.7 | 96.0% |
| D1 | $BPO_4SiO_2$ | " | 13.3 | 95.2% |
| E1 | $BPO_4/C$ | " | 2.2[4] | 53.2%[4] |
| F1 | $B_2(SO_4)_3/SiO_2$ | " | 5.5 | 87.9% |
| A2 | $SiO_2$ | 0.43 | 12.0 | 94.4% |
| A3 | $SiO_2$ | 0.60 | 10.4 | 93.4% |
| B2 | $BPO_4$ | 0.50 | 11.5 | 94.5% |
| C2 | $BPO_4/SiO_2$[1] | " | 16.5 | 96.2% |
| D2 | $BPO_4/SiO_2$[2] | " | 31.7 | 97.9% |
| E2 | $BPO_4/C$ | " | 35.5 | 95.4% |
| F2 | $B_2(SO_4)_3/SiO_2$ | " | 25.0 | 97.0% |
| A4 | $SiO_2$ | 0.71 | 3.4 | 86.3% |
| B3 | $BPO_4$ | 0.75 | 8.6 | 92.7% |
| C3 | $BPO_4/SiO_2$[1] | " | 11.6 | 94.5% |
| D3 | $BPO_4/SiO_2$[2] | " | 31.8 | 97.9% |
| E3 | $BPO_4/C$ | " | 60.0 | 97.5% |
| F3 | $B_2(SO_4)_3/SiO_2$ | " | 21.1 | 96.7% |
| A5 | $SiO_2$ | 1.00 | 11.9 | 94.6% |
| B4 | $BPO_4$ | " | 11.2 | 94.1% |
| C4 | $BPO_4/SiO_2$[1] | " | 17.0 | 96.0% |

[1]containing 27 weight-% $BPO_4$
[2]containing 65 weight-% $BPO_4$
[3]%-yield of cyclohexane divided by %-conversion of methylcyclopentane × 100
[4]results believed to be erroneous (likely reason: contamination of catalyst or feed)

Test data in Table I clearly show that the $AlCl_3/BPO_4SiO_2$, $AlCl_3/B_2(SO_4)_3/SiO_2$ and $AlCl_3/BPO_4/C$ catalyst materials were generally more effective (in terms of feed conversion and selectivity to cyclohexane) than $AlCl_3/SiO_2$ and $AlCl_3/BPO_4$, in particular at the more preferred $AlCl_3$:support weight ratio of 0.50:1 to 1.00:1.

Reasonable variations, modifications and adaptations for various conditions and reactants can be made within the scope of the disclosure and the appended claims without departing from the scope of this invention.

That which is claimed is:

1. A process for isomerizing cycloalkanes which comprises contacting, at a reaction temperature of about 0°-100° C., at least one cycloalkane containing 5-10 carbon atoms per molecule with a solid catalyst composition at effective isomerization conditions, wherein said catalyst composition has been prepared by a method comprising the steps of (I) heating in the substantial absence of water, at a temperature of about 40°-90° C., a mixture comprising (a) aluminum chloride, (b) at least one solid boron-containing material selected from the group consisting of boron phosphate on silica, boron phosphate on activated carbon and boron sulfate on silica, and (c) at least one chlorinated hydrocarbon having a normal boiling point of about 40°-90° C., wherein the weight ratio of aluminum chloride to said at least one solid boron-containing material is at least about 0.25:1; and (II) separating the solid material contained in the reaction mixture obtained in step (I) from said at least one chlorinated hydrocarbon under a dry gas atmosphere.

2. A process in accordance with claim 1, wherein said at least one chlorinated hydrocarbon is carbon tetrachloride.

3. A process in accordance with claim 2, wherein the ratio of the weight of carbon tetrachloride to the combined weight of materials (b) and (b) in step (I) is about 4:1 to about 20:1.

4. A process in accordance with claim 2, wherein said at least one solid boron-containing material is selected from the group consisting of boron phosphate on silica and boron sulfate on silica, and the content of silica in said solid boron-containing material is about 20-80 weight-% $SiO_2$.

5. A process in accordance with claim 4, wherein the weight ratio of aluminum chloride to said at least one solid boron-containing material is about 0.25:1 to about 1.0:1.

6. A process in accordance with claim 4, wherein said at least one solid boron-containing material is boron phosphate on silica having been prepared by reacting at least one boric acid ester and orthopbosphoric acid in the presence of silica, distilling off the liquids from the reaction mixture, drying the thus-obtained solid material, and calcining the dry solid material at a temperature of about 250°-500° C.

7. A process in accordance with claim 4, wherein said at least one boron-containing support material is boron sulfate on silica having been prepared by reacting at least one boric acid ester with sulfuric acid, distilling off liquids from the reaction mixture, drying the thus-obtained solid support material, and calcining the dry solid support material at a temperature of about 250°-500° C.

8. A process in accordance with claim 2, wherein said at least one solid boron-containing material is boron phosphate on activated carbon and the content of carbon in said solid boron-containing material is about 20-80 weight-% C.

9. A process in accordance with claim 8, wherein the weight ratio of aluminum chloride to said at least one boron-containing support material is about 0.5:1 to about 1.0:1.

10. A process in accordance with claim 8, wherein said at least one solid boron-containing material has been prepared by reacting at least one boric acid ester with phosphoric acid in the presence of activated carbon, distilling off liquids from the reaction mixture, drying the thus-obtained solid material, and calcining the dry solid material at a temperature of about 250°-500° C.

11. A process in accordance with claim 1, wherein the surface area of said at least one solid boron-containing material is about 100-1000 $m^2/g$.

12. A process in accordance with claim 1, wherein heating step (I) is carried out for about 5-30 hours under a dry inert gas atmosphere, and step (II) is carried out under an inert gas atmosphere in two sub-steps filtering the reaction mixture formed in step (I) so as to recover the solid component therefrom and then drying the recovered solid material.

13. A process in accordance with claim 1, wherein said effective isomerization conditions comprise a reaction temperature of about 20°-50° C. and a reaction time of about 0.1-8 hours.

14. A process in accordance with claim 13, wherein said at least one cycloalkane is methylcyclopentane.

* * * * *